United States Patent
Bacino et al.

[11] Patent Number: 5,878,758
[45] Date of Patent: Mar. 9, 1999

[54] DENTAL FLOSS ARTICLE

[75] Inventors: John Edward Bacino, Avondale; John W. Dolan, Boothwyn, both of Pa.; Thomas Michael Gray, Middletown, Del.

[73] Assignee: Gore Enterprise Holdings, Inc., Newark, Del.

[21] Appl. No.: 926,719

[22] Filed: Sep. 10, 1997

Related U.S. Application Data

[62] Division of Ser. No. 641,102, Apr. 26, 1996, Pat. No. 5,718,251.

[51] Int. Cl.$^6$ .................................................... A61C 15/00
[52] U.S. Cl. ............................................ 132/321; 132/329
[58] Field of Search ................................... 132/321, 323, 132/324, 325, 326, 327, 328, 329; 606/228, 229, 230, 231

[56] References Cited

U.S. PATENT DOCUMENTS

| | | | |
|---|---|---|---|
| 2,522,794 | 9/1950 | Medof | 132/325 |
| 3,699,979 | 10/1972 | Muhler et al. | |
| 3,744,499 | 7/1973 | Wells | |
| 3,771,536 | 11/1973 | Dragan | |
| 3,830,246 | 8/1974 | Gillings | |
| 3,930,059 | 12/1975 | Wells | 132/321 |
| 3,953,566 | 4/1976 | Gore | |
| 4,008,727 | 2/1977 | Thornton | |
| 4,011,658 | 3/1977 | Tarrson et al. | |
| 4,029,113 | 6/1977 | Guyton | |
| 4,034,763 | 7/1977 | Frazier | |
| 4,034,771 | 7/1977 | Guyton | |
| 4,142,538 | 3/1979 | Thornton | |
| 4,270,556 | 6/1981 | McAllister | |
| 4,280,500 | 7/1981 | Ono | |
| 4,372,293 | 2/1983 | Vijil-Rosales | |
| 4,414,990 | 11/1983 | Yost | |
| 4,450,849 | 5/1984 | Cereco et al. | |
| 4,693,365 | 9/1987 | Corella | |
| 4,776,358 | 10/1988 | Lorch | |
| 4,832,063 | 5/1989 | Smole | |
| 4,836,226 | 6/1989 | Wolak | |
| 4,985,296 | 1/1991 | Mortimer, Jr. | |
| 4,996,056 | 2/1991 | Blass | |
| 4,998,978 | 3/1991 | Varum | |
| 5,033,488 | 7/1991 | Curtis et al. | |
| 5,063,948 | 11/1991 | Lloyd | |
| 5,098,711 | 3/1992 | Hill et al. | |
| 5,209,251 | 5/1993 | Cutis et al. | |
| 5,220,932 | 6/1993 | Blass | |
| 5,226,434 | 7/1993 | Britton et al. | |
| 5,226,435 | 7/1993 | Shonen et al. | |
| 5,274,074 | 12/1993 | Tang et al. | |
| 5,284,169 | 2/1994 | Gilligan et al. | 132/321 |
| 5,289,836 | 3/1994 | Peng | 132/321 |
| 5,305,768 | 4/1994 | Gross et al. | |
| 5,320,117 | 6/1994 | Lazzara et al. | |
| 5,340,581 | 8/1994 | Tseng et al. | |
| 5,353,820 | 10/1994 | Suhonen et al. | 132/321 |
| 5,357,989 | 10/1994 | Gathani | |
| 5,383,904 | 1/1995 | Totakura et al. | |
| 5,454,834 | 10/1995 | Boebel et al. | |
| 5,518,012 | 5/1996 | Dolan et al. | |
| 5,560,377 | 10/1996 | Donovan | 132/321 |
| 5,566,691 | 10/1996 | Dolan et al. | 132/321 |

FOREIGN PATENT DOCUMENTS

| | | |
|---|---|---|
| 335466 | 10/1989 | European Pat. Off. |
| 451729 | 5/1991 | European Pat. Off. |
| 0 750 902 | 1/1997 | European Pat. Off. |
| 2128133 | 4/1984 | United Kingdom |
| 2258402 | 2/1993 | United Kingdom |
| 9210978 | 9/1992 | WIPO |
| 9506447 | 3/1995 | WIPO |
| 9534252 | 12/1995 | WIPO |
| 9610478 | 4/1996 | WIPO |

*Primary Examiner*—Gene Mancene
*Assistant Examiner*—Philogene Pedro
*Attorney, Agent, or Firm*—Allan M. Wheatcraft

[57] ABSTRACT

A dental floss article is provided comprising a fiber having a predetermined length and defined by at least one substantially rigid portion and at least one flexible portion.

7 Claims, 5 Drawing Sheets

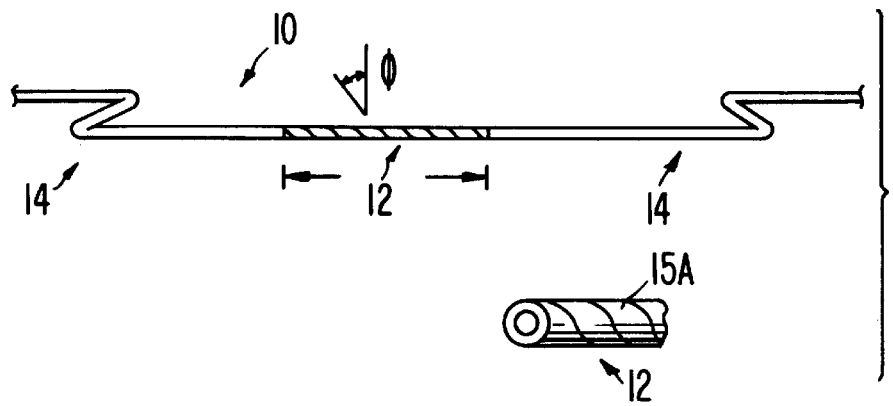
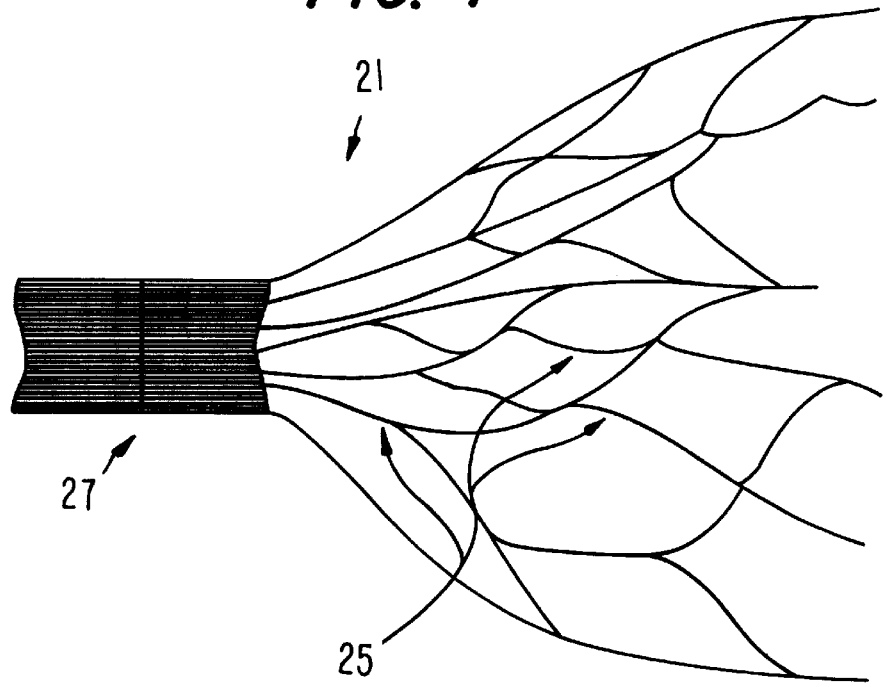
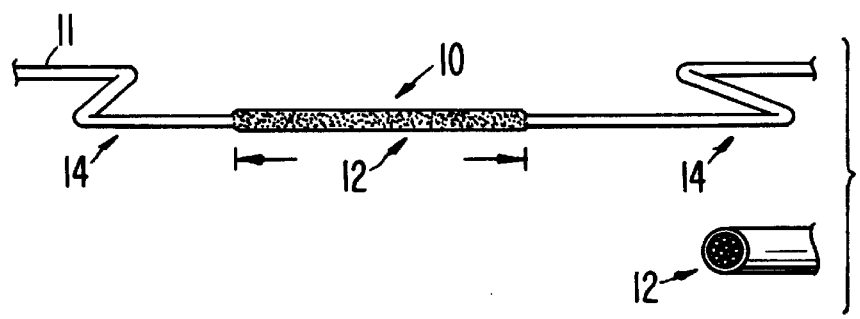

DENTAL FLOSS ARTICLE

CROSS REFERENCE TO RELATED APPLICATION

This application is a divisional application of Ser. No. 08/641,102, filed Apr. 26, 1996, now U.S. Pat. No. 5,718,251.

FIELD OF THE INVENTION

The present invention relates to a dental floss article for promoting oral hygiene.

BACKGROUND OF THE INVENTION

It is well understood that the use of dental floss is an important part of a total oral hygiene program. Flossing teeth helps to prevent periodontal disease, such as gingivitis for example. The use of floss helps to dislodge food particles and plaque from interstitial surfaces of teeth. Caries will develop on tooth surfaces where there is an accumulation of plaque. Although the use of a toothbrush reduces plaque on the occlusal areas of teeth, a tooth brush offers only a minimal reduction in plaque within the interstitial regions of the teeth. Dental floss is the only effective means to disrupt the accumulation of plaque in such interstitial regions, thereby reducing the likelihood for the carie development.

Unfortunately, persons requiring fixed orthodontic appliances, commonly referred to in the United States as braces, and persons wearing dental bridges, such as a Maryland style bridge for example, can not benefit from the cleaning capabilities associated with normal dental flossing techniques without the aid of cumbersome apparatus. More particularly, standard flossing techniques are not appropriate for users of these appliances and devices because they prevent the dental floss from freely entering into the interstitial regions when performing the normal up and down motion of flossing.

In the past, a floss threader or needle has been employed to thread dental floss between a gum line and an orthodontic appliance or Maryland bridge. One such floss threader is disclosed in U.S. Pat. No. 4,011,658. A shortcoming of such a floss threader is that it is often very cumbersome to use, especially for a person lacking average dexterity. A user of such a floss threader must thread the device prior to application in the mouth for the purposes of flossing, much like a sewing needle.

Another shortcoming associated with the use of a floss threader is the potential for the device to be swallowed during use if the threader becomes separated from the floss. Children may lack the motor skills to remove the separated pieces from their mouth, which, of course, is hazardous.

Attempts have been made to bond a rigid floss leader to a flexible section of dental floss. Such an article is disclosed in U.S. Pat. No. 4,832,063. However, the bond between the two units often fails in use. Additionally, an enlarged cross-sectional diameter at the transition point between the leader and the floss may cause pain when passing the article through the space between the teeth and gums.

As disclosed in U.S. Pat. No. 3,744,499, a plastic coating may be applied to a dental floss to render a portion of the dental floss rigid. Although this method may be satisfactorily employed with dental floss materials consisting of thermoplastics, such as nylon or polyethylene, and natural fibers such as cotton, such a method is not useful with dental floss comprised at least in part of polytetrafluoroethylene (PTFE). When such a method is practiced on non-modified monofilaments of polytetrafluoroethylene, expanded polytetrafluoroethylene, or full density expanded polytetrafluoroethylene, the molten thermoplastic beads on the surface of the dental floss material and does not provide a rigid continuous network of the thermoplastic. The beading of the thermoplastic is due to the inherent low surface energy and high hydrophobicity of the polytetrafluoroethylene.

The use of polytetrafluoroethylene as a dental floss is taught in such United States Patents as U.S. Pat. Nos. 5,033,488 and 5,220,932. It is well accepted that dental flosses made of polytetrafluoroethylene and forms of expanded porous polytetrafluoroethylene are superior to nylon and natural fiber materials. Flosses consisting of PTFE benefit from the low coefficient of friction inherent to PTFE thereby allowing the floss material to easily maneuver between tight oral contacts without excessive force or severe abrading of gum tissue. Notwithstanding the laudable benefits associated with dental flosses comprised at least in part of PTFE, to date, secondary floss threader devices are needed by persons having orthodontic appliances or dental bridges, and who wish to use such PTFE dental floss.

The foregoing illustrates limitations known to exist in present dental floss materials. Thus, it is apparent that it would be advantageous to provide an improved dental floss article directed to overcoming one or more of the limitations set forth above. Accordingly, a suitable alternative is provided including features more fully disclosed hereinafter.

SUMMARY OF THE INVENTION

The present invention advances the art of dental floss articles, and the techniques for creating such dental floss articles, beyond which is known to date. In one embodiment of the present invention, a dental floss article is provided comprising a hydrophobic fiber having a predetermined length. The hydrophobic fiber is defined by at least one substantially rigid portion and at least one flexible portion. The at least one substantially rigid portion is defined by a rigidifying member that is made integral with the hydrophobic fiber such that the hydrophobic fiber completely encapsulates the rigidifying member. The hydrophobic fiber may be expanded porous polytetrafluoroethylene (ePTFE) or ultra high molecular weight polyethylene, for example.

In another embodiment of the present invention, a dental floss article is provided comprising a hydrophobic fiber having a predetermined length. The hydrophobic fiber is defined by at least one substantially rigid portion and at least one flexible portion. The at least one substantially rigid portion is defined by a polymeric coating or covering that is made integral with the hydrophobic fiber such that a length of the hydrophobic fiber is completely encapsulated by said polymeric coating or covering. The hydrophobic fiber may be a monofilament or a towed fiber of expanded porous polytetrafluoroethylene (ePTFE) or ultra high molecular weight polyethylene, for example. The polymeric covering may be a tube or a tape wrapping.

In another embodiment of the present invention, a method is provided for producing a dental floss article comprising the steps of: providing a porous polymeric fiber having a predetermined length; filling a monomer within the fiber at a predetermined location along the length of said fiber; and polymerizing the monomer in place within said porous polymeric fiber, thereby rendering said filled location substantially more rigid than an unfilled region.

In yet another embodiment of the present invention a dental floss article is provided comprising a towed fiber of a fluoropolymer or polyolefin material. The towed fiber may be expanded porous polytetrafluoroethylene or ultra high molecular weight polyethylene, for example.

The teachings of the present invention may also be employed to produce an improved suture.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings:

FIG. 3 is an isometric view of a dental floss article of the present invention having a semi-rigid section formed by wrapping heat shrinkable tape around a fiber;

FIG. 4 is a planer view of a dental floss article comprising a 1200 denier towed fiber in accordance with one embodiment of the present invention;

FIG. 5 is an isometric view of a dental floss article of the present invention having a semi-rigid section formed by coating and curing a polymeric material onto towed portions of the dental floss article of FIG. 4;

DETAILED DESCRIPTION OF THE INVENTION

Figure 1:
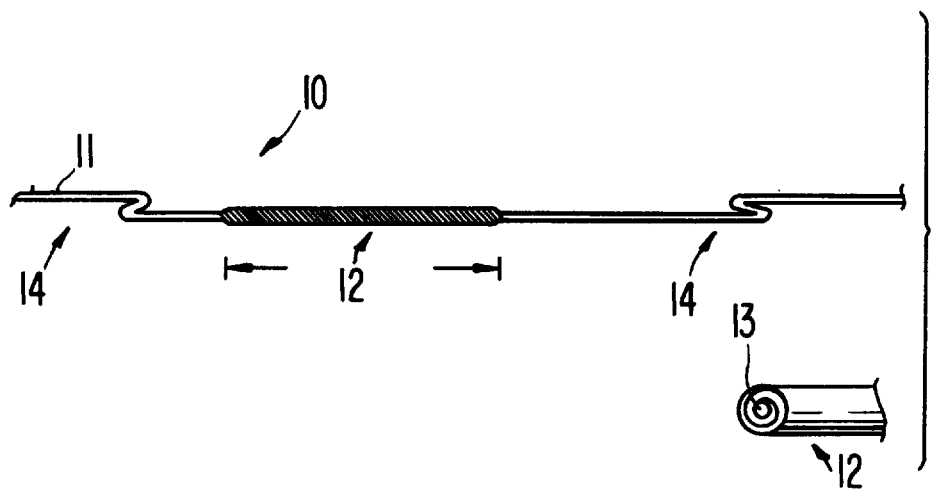
FIG. 1 is an isometric view of a dental floss article of the present invention having a semi-rigid section formed by wrapping and bonding a fiber around a stiffening material.

Referring now to the drawings, one embodiment of the dental floss article of the present invention is generally illustrated at 10 in FIGS. 1, 2, 3, and 5. Such a dental floss article comprises a hydrophobic fiber, such as an expanded porous polytetrafluoroethylene (ePTFE) fiber 11, that defines at least one semi-rigid portion 12 and at least one flexible portion 14. The dental floss article 10 may be rolled, or otherwise disposed on a bobbin-like apparatus, and may be placed on a supporting core so that it may be easily integrated within a suitable dispensing apparatus (not shown). Alternatively, the dental floss article may be defined by a single use length which includes a single semi-rigid portion 12 and a single flexible portion 14; such a floss apparatus may be packaged in a single use sterile package.

As the term is used herein, expanded porous polytetrafluoroethylene (ePTFE) shall mean a membrane which may be prepared by any number of known processes, for example, by stretching or drawing processes, by papermaking processes, by processes in which filler materials are incorporated with the PTFE resin and which are subsequently removed to leave a porous structure, or by powder sintering processes. Preferably, the porous polytetrafluoroethylene membrane is porous expanded polytetrafluoroethylene membrane having a microstructure of interconnected nodes and fibrils, as described in U.S. Pat. Nos. 3,953,566; 4,187,390; and 4,110,392, which are incorporated herein by reference, and which fully describe the preferred material and processes for making them. The expanded porous polytetrafluoroethylene membrane may be produced in filament form, such a form is preferred.

Figure 8:
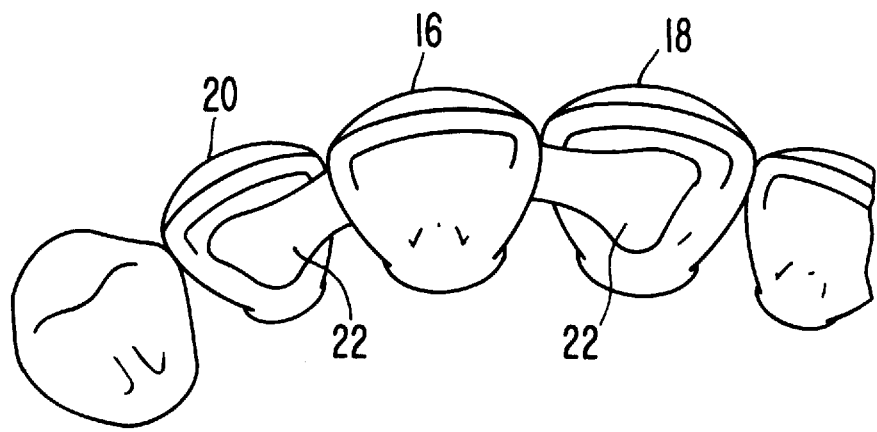
FIG. 8 is an isometric view of a dental bridge.
Figure 9:
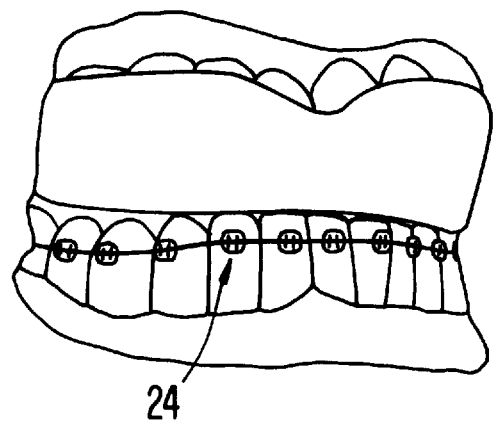
FIG. 9 is a view of a fixed orthodontic appliance (braces).

As best illustrated by FIG. 8, a typical bridge comprises a pontic or false tooth 16, which is anchored by natural teeth 18 and 20 by way of metal supports 22. The semi-rigid portion 12 of the dental floss article 10 facilitates insertion thereof between the teeth, preferably at the gum line, thereby acting as a leader for the flexible portion 14. As best illustrated by FIG. 9, the semi-rigid portion 12 also facilitates insertion of the dental floss article 10 between the interstitial regions of teeth in cases where the person has fixed orthodontic appliances, such as braces 24.

As the term "floss" is used herein, it is intended to encompass a thread-like material suitable for facilitating oral prophylaxis. Although the present invention is described in one embodiment as a dental floss article, it is contemplated that the article of the present invention may provide an excellent improved suture for use in various surgical applications. Accordingly, such an embodiment as a suture is fully contemplated by the teachings herein.

As should be understood, a preferred fiber 11 for use in the dental floss article 10 is a fiber of ePTFE. However, it is contemplated that the teachings of the present invention may be employed with other fibers such as polyolefins (e.g. ultra high molecular weight polyethylene), polyamides, polyimides, polyurethanes, elastomeric materials, polymer blends, or natural fibers, for example.

In one embodiment of the present invention illustrated in FIG. 1, the dental floss article 10 is defined by semi-rigid portions 12, comprised of an internal stiffener, stiffening member or rigidifying member 13 that is adhesively bonded to and wrapped within the expanded polytetrafluoroethylene (ePTFE) fiber 11. Flexible portions 14 are comprised of the ePTFE fiber 11 which may also be wrapped or folded onto itself. By wrapping the stiffener 13 within the ePTFE fiber 11, an unexpected improvement is achieved. The well known low coefficient of friction for the ePTFE material improves the feel or slide of the stiffener through a persons teeth while providing additional strength and support to the stiffener to resist buckling forces due to the frictional force created when passing the stiffener through an interproximal area. As should be understood, such an embodiment of the present invention completely encapsulates a stiffening member, thereby rendering the otherwise limp expanded PTFE fiber 11 semi-rigid. Also, such an embodiment of the present invention does not create an abrupt change in the cross-sectional area of the dental floss article between the stiffened portion 12 and the flexible portion 14, thereby providing comfort to a user of the dental floss article 10. Also, by completely encapsulating the stiffening member 13, the possibility that the stiffening member will separate from the ePTFE fiber is reduced. The encapsulation of the stiffening member also provides additional tensile strength and stiffness to the semi-rigid portion 12.

Great tailorability is afforded to the dental floss article 10 by using a wide variety of stiffeners such as polymers, metals, etc., and any suitable adhesive for bonding the stiffeners with the ePTFE fiber 11. The ePTFE fiber can be a monofilament, laminate, twist, braid or filled product to offer further tailorability to the stiffened section, as well as to the properties of the dental floss. Coloring may be added to the dental floss article 10 to help identify either the semi-rigid portion 12 of the floss, or the the flexible portion 14, or both. A preferred stiffener is a single, flexible, nylon filament approximately 12 to 125 mm in length, and most preferably approximately 50 to 80 mm in length. The stiffener may have any suitable dimensional characteristics including, but not limited to, round, square, rectangular or triangular cross sections, for example. However, a round cross section is preferred. The stiffener may be of various suitable diameters, preferably from 0.35 to 0.55 mm. The adhesive can be any suitable form such as a transfer adhesive, cyano acrylate, epoxy, hot melt adhesive, UV cure adhesive, or silicone, and most preferably a hot melt or UV cure adhesive system.

The stiffness of the semi-rigid portion 12 of the dental floss article 10 is a critical factor in that if a leader, or threader end of the article is too stiff, it becomes very difficult and painful to maneuver the semi-rigid portion 12 through the back region of an occlusal site. However, some degree of flexibility is required in the semi-rigid portion 12 so that a user can easily divert a tip of the semi-rigid portion towards the front of his or her mouth, using the tongue, thereby permitting the user to capture the semi-rigid portion with the fingers and pull the trailing flexible portion 14 into a desired location for the flossing activity.

Figure 2:
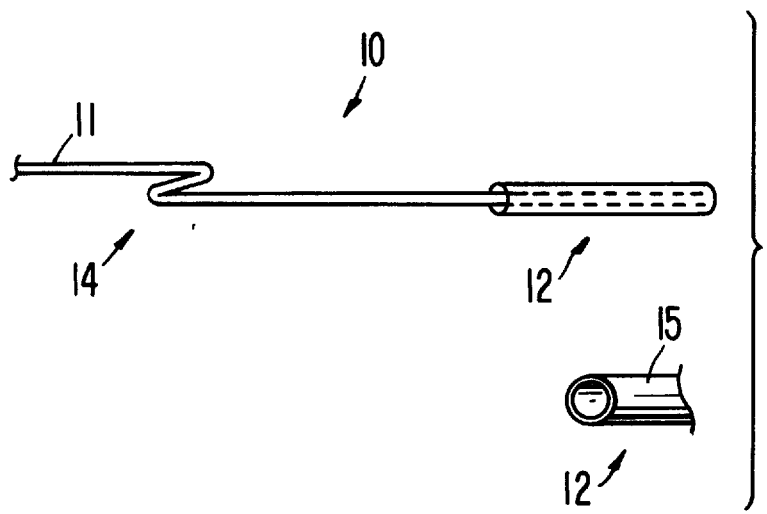
FIG. 2 is an isometric view of a dental floss article of the present invention having a semi-rigid section formed by wrapping heat shrinkable tubing around a fiber.

In another embodiment of the present invention illustrated in FIG. 2, the semi-rigid portion 12 may be formed by the use of heat shrinkable tubing 15. For example, various polymer tubing is available, which upon heating to an appropriate temperature, will relax and shrink upon itself and any object placed internal to the tube. Any number of heat shrinkable tubings are suitable, such as but not limited to, polytetrafluoroethylene, fluorinated ethylene propylene (FEP), low density polyethylene, polyvinylchloride, or polyester.

As illustrated in FIG. 3, in another embodiment of the present invention, the stiffening of a section of fiber 11 may also be accomplished by tape wrapping a sheet or film 15A of shrink type material onto the fiber 11, followed by heating to allow consolidation of the sheet or film. This may be accomplished by using a helical tape wrap pattern, or a straight lap tape wrap similar to the tape wrap of a commercially available shoe string end. A wrap angle φ may be from 0 to 85 degrees, with a preferred range of 0 to 45 degrees. The wrap material may consist of a variety of polymeric and metallic tape or ribbon materials, but a preferable material is PTFE and expanded PTFE for its low coefficient of friction properties. If a more aggressive bond is required, the tape wrap may be FEP.

In another embodiment of the present invention, the semi-rigid portion of the dental floss article 10 can be achieved by the incorporation of a center core of polymeric or metallic material within the cross-section of an ePTFE fiber. This incorporation can be easily accomplished during the production of the ePTFE fiber and is similar to insertion molding. The incorporated filament material is intermittently introduced at or near a converging extrusion die prior to the area where a PTFE extrudate exits the extrusion die. The extruded PTFE material forms around the incorporated material. The incorporated material provides for regions where the article is substantially stiffer than other areas of the article. Heat and pressure may be used to render the incorporated areas even stiffer as compared to the article stiffness prior to the heat and pressure operation. An enhancement to this embodiment is realized if the incorporated filament material is made of a polymeric material, such that the material is not intermittently introduced as described above but rather, is continuously incorporated within the cross-section of the PTFE extrudate. As it is well known in the art of the production of expanded porous PTFE, the matrix tensile strength of extruded PTFE material is substantially increased as the material is expanded, as described in U.S. Pat. No. 3,953,566. The substantial increase of the matrix tensile strength of the expanded porous PTFE, over the non-expanded PTFE, is greatly desired in that the overall tensile strength of a floss article or device should be sufficient so that in normal use of the floss article, the article or device does not break in the users teeth due to the lack of tensile strength of the floss article or device. In converting the PTFE extrudate into a form of expanded porous PTFE, and especially a coextrusion of PTFE where the PTFE is coextruded with a polymeric material (e.g. nylon) within the cross-section of the PTFE matrix, an unexpected result is realized if sections of the continuous coextrusion are prevented from undergoing a transformation, from non-expanded PTFE to expanded porous PTFE, and other sections of the coextrusion are converted into forms of expanded porous PTFE. The non-expanded regions of the coextrusion are substantially more rigid than the expanded regions in that, the polymeric material incorporated within the PTFE matrix becomes extremely thin as the expanded sections are stretched. The stiffing effect of the incorporated polymeric filament material is thus substantially minimized as the polymeric material cross-sectional area becomes small and therefore, looses its geometrical presence within the ePTFE matrix. As it is well known, if PTFE undergoes an uniaxial expansion operation using certain known conditions of temperature and expansion rate, the density of the PTFE decreases as the linear length increases, yielding an extremely strong filament which is not susceptible to shredding. The presence of the incorporated polymer filament is only realized in the semi-rigid portions where the extrudate did not undergo an expansion operation. Regions of the extrudate can easily not undergo the expansion process by expanding the coextrusion material between two nip rollers. For regions where the less stiff portions are desired, the second of the two nip rollers rotate at a faster surface velocity than the first, thereby creating tension on the extrudate restrained between the two nips. For regions where the portion is desired to be more stiff than the expanded sections, the second nip roller assembly has the same surface velocity as the first nip roller assembly thus creating no tension in the extrudate, hence no stretching occurs. The semi-rigid sections can be further enhanced by application of heat and pressure over the stiff sections thereby thermally and mechanically manipulating the incorporated polymeric material thus providing for a better bond and either maintaining or conforming the semi-rigid section to a desirable geometric configuration. Such geometric configurations for the semi-rigid section include, but are not limited to, a semi-curve-linear form, straight sword type form, or a compound angular form. It is preferred that the semi-rigid section contain at least some curvature similar to an upholstery needle since the curvature permits the user to easily grasp the semi-rigid section after the user places the device through his teeth.

In another embodiment of the present invention, a semi-rigid portion 12 may be achieved by the incorporation of a monomer within the matrix of the expanded porous PTFE, and then subsequently polymerizing the monomer in place within the ePTFE matrix, thereby rendering the filled region substantially more stiff than the unfilled regions. The monomer when polymerized or cured consists of a material whose modulus of elasticity is higher than that of expanded PTFE, such that when used in a composite construction of the two materials, the polymerized incorporated material provides for a significant increase of the overall modulus of elasticity of the composite structure. The increase of the modulus of elasticity is realized by the user as an increase in stiffness of the fiber 11.

The incorporated monomer material can be dissolved into a solvent. The viscosity of the solvent and monomer mixture should be very low so that it can easily be placed into the porous matrix of the expanded PTFE. It is preferred that the solvent has an overall oil rating number of two or less, such that it can easily be placed into the ePTFE matrix. For materials with higher oil rating numbers, difficulty is shown when placing these materials into the ePTFE matrix due to the extremely low surface energy of the ePTFE. Surface modifications, such as corona treating or plasma treating, can be applied to the ePTFE to increase the hydrophilic nature of the material, thus making the ePTFE more receptive for solvent filling.

Other methods for incorporating the monomer into the ePTFE matrix may include vacuum disposition or coextrusion. The incorporated monomer can be polymerized by several mechanisms which are particular to the monomer used. Polymerization initiation can be UV, thermal, pressure (i.e. shear gradient), or chemically activated. Typical activated materials include thermosets and epoxy polymers, where thermosets are cured using a temperature gradient and epoxies are cured by chemical interaction.

The high temperature stability of the base PTFE structure provides for an excellent carrier for the incorporation of a thermoset during blending of raw PTFE powder prior to extrusion. After the coextrusion extrudate has been converted into a form of expanded PTFE, the thermoset can be cured or polymerized at desired locations, thus providing for semi-rigid and non-rigid sections of the dental floss article. This method of blending the curable or the polymerizable monomer with the raw PTFE powder negates the potential shortcoming associated with the inherent high hydrophobicity of PTFE. As mentioned previously, the high hydrophobicity prevents viscous solvents, especially viscous solvents with high surface energies, from being easily placed or absorbed into the porous expanded PTFE matrix.

In yet another embodiment of the present invention, extremely fine particles of a thermoplastic polymer can be introduced into the fibril-node structure of the ePTFE, followed by a curing operation to melt and reflow the polymers to make a continuous network within the matrix of the ePTFE thereby stiffening the fiber in desired locations.

As illustrated in FIG. 5, another embodiment of the present invention, the semi-rigid portion 12 can be formed by application of a polymer coating or dispersion to the fiber 11 in selected predetermined locations, followed by curing of the polymer to a semi-rigid state. For example, suitable polymer dispersions may include, but are not limited to, polytetrafluoroethylene (PTFE), fluorinated ethylene-propylene (FEP), and polyvinylidene fluoride (PVDF). Though application of these polymers to the fiber alone will create some degree of adherence, it is important to modify the surface of the fiber to promote a much more tenacious bond. This surface preparation can be accomplished by a variety of techniques including, but not limited to, mechanical, chemical, or electrochemical means, such as roughening the surface with sandpaper, treatment with an etchant, or by corona surface modification treatment. A preferred technique is to use a fully towed fiber, or to intermittently "tow" a 12 to 125 mm, preferably 50 to 80 mm, section of an ePTFE fiber, approximately every 0.5 meters along the length. The towing operation consists of running the fiber 11 over a rotating pinwheel to create a "tow yarn". As shown in FIG. 4, a tow yarn 21 is a lattice structure of long randomly interconnected filaments 25 of ePTFE making up a continuous fiber 27. As shown in FIG. 5, the tow yarn 21 is then coated with a polymer in predetermined locations, followed by curing for an appropriate time and at an appropriate temperature, for the particular polymer used, to form a semi-rigid section 12. In doing so, the polymer has much greater surface area to bond with during polymerization, and at the same time mechanically locks the tow filaments together with a continuous network of polymer to form one continuous semi-rigid desired section. The shape and texture of the semi-rigid portion 12 can be manipulated by processing the polymer containing end through a molding die while still in the semi-viscous state. In doing so, one can achieve different end characteristics suitable and desired for guiding the floss through the interstices between the teeth and gums of the user. The color too can be manipulated by placing desired pigments into the polymer prior to the coating or dipping process thus helping the user to identify the semi-rigid sections to be used as the treading device of this article.

To enhance gripping of the dental floss article of the present invention, the article may be in part or in total, coated with a layer of wax. The wax may be any suitable wax such as carnuba, natural beeswax, candelilla, petroleum wax, synthetic petroleum wax, oxidized polyethylene, or micro crystalline. It has been found that a wax coating of from 0.5% to about 20% by weight is achievable, but a coating of 2 to 10% is preferable.

The dental floss article of the present invention may be waxed using standard lick roller type waxing machines. The article may also be waxed using a number of liquid wax spray techniques such as those used for application of waxes on citrus fruit or other produce. The article may also be dip coated in a molten bath of wax. In addition to enhanced grippability of the dental floss article, the wax may be used to cover, or to carry an assortment of materials on the dental floss article to be delivered to the mouth and teeth. These materials may include, but are not limited to, flavoring oils, whiteners, abrasives, anti-bacterials, anti-tarter agents, or medicaments, such as, tetracycline, iodine, vitamins, etc.

Figure 6:
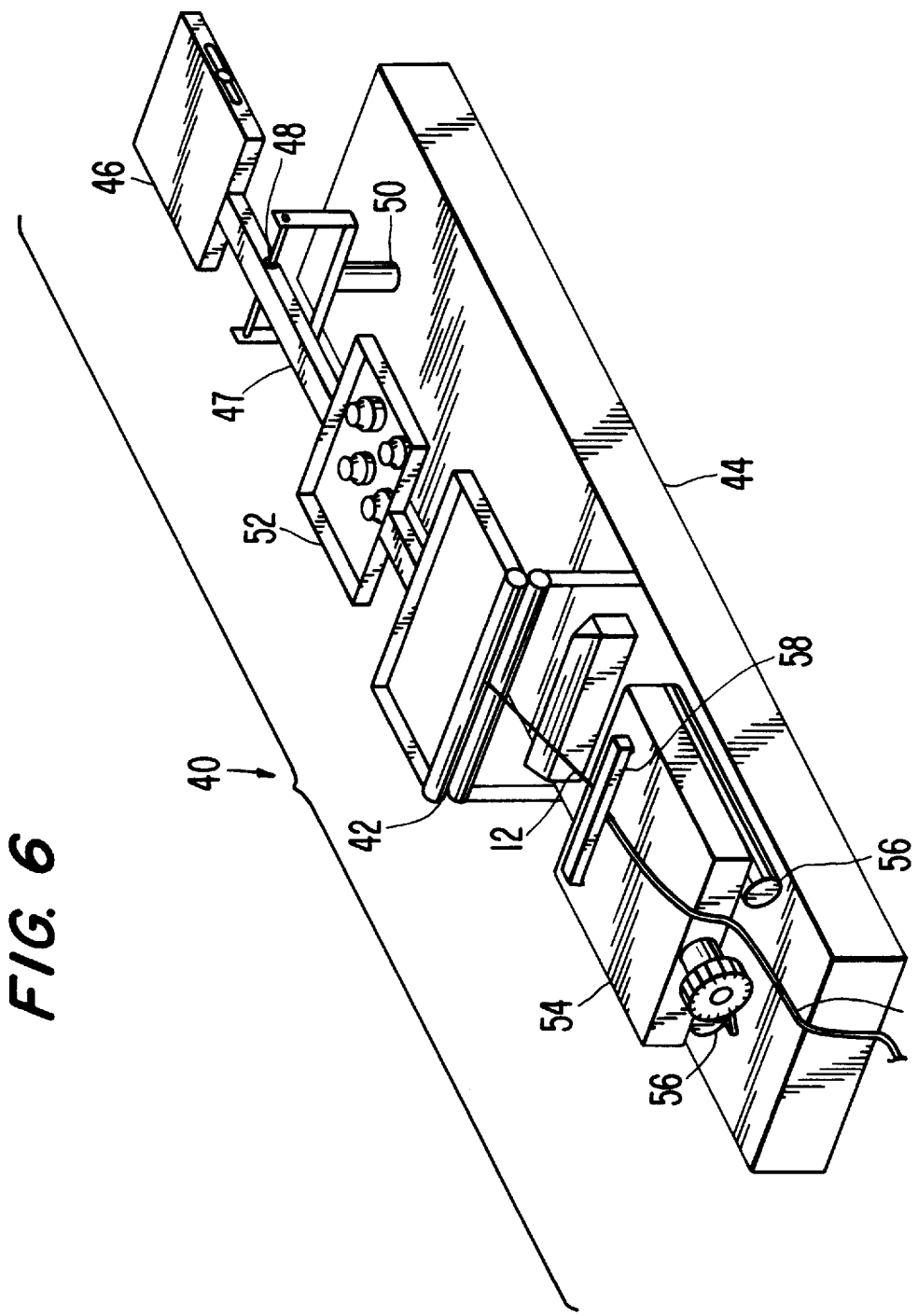
FIG. 6 is an isometric view of a test apparatus used to determine a resistance to buckling loads of various semi-rigid materials.

As best seen by reference to FIG. 6, a testing apparatus 40 was developed and built to determine the stiffness of the semi-rigid portion 12. The testing apparatus comprises an artificial dental contact site made from two parallel adjacent 6.35 mm glass stirring rods 42, approximately 50 mm long. The bottom glass rod is stationary and fixed to a base 44 while the top glass rod is mounted to a lever arm 47 that is counterbalanced by member 46 and free to pivot about its bearing 48. The bearing is fixed to an anvil 50 which is stationary and fixed to the base 44. A load can be applied to the glass contacts by placing various weights into a load tray 52. A stiffened fiber or threading device 12 is presented perpendicular to the glass contacts and guided so that a tip of the semi-rigid portion meets a tangent line between the two glass rods. The fiber is mounted to a tray assembly 54 which travels along two guide rails 56 and is fixed to the tray by clamp 58, 25 mm behind the tip, exposing 25 mm of the semi-rigid portion. The tray assembly is then hand cranked moving the fiber horizontally into the glass contact point 42. The semi-rigid portion will either lift the contacts and penetrate through, or buckle from the applied load.

Figure 7:
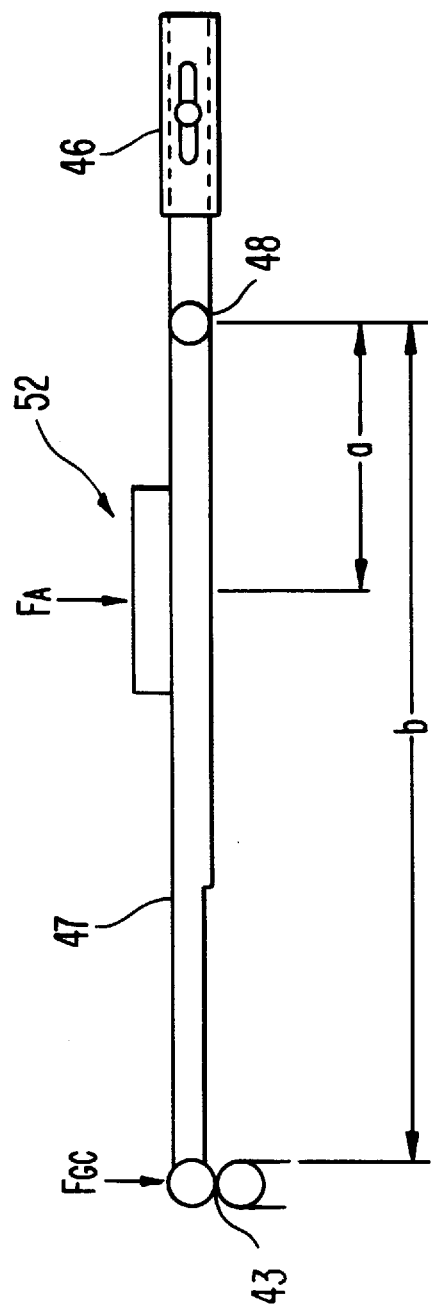
FIG. 7 is a side view of a lever arm of the test apparatus of FIG. 6.

Referring to FIG. 7, the load tray 52 is mounted with its center 50 mm away from the pivot point of the bearing 48, distance "a". The glass rod contact point 43 is 150 mm away from the bearing, distance "b". For the purpose of calculating the applied load at the glass contact point, which will cause a fiber to buckle rather than force the two glass rods apart, the mass applied to the load tray 52 is assumed to be centrally located in the tray above the center line of the lever arm 47. This allows for the calculation that, $F_{GC}=F_A(a)/b$. The load to resist buckling $F_{GC}$ of different fibers can be quantified in this fashion. A range of 3 to 1200 grams has been determined to be suitable for the semi-rigid portion, as measured by the testing apparatus, with a preferred range of 10 to 60 grams.

Without intending to limit the scope of the present invention, the apparatus and method of production of the present invention may be better understood by referring to the following examples:

EXAMPLE 1

2200 denier flat ePTFE fiber (obtained from W. L. Gore and Associates, Inc., Elkton, Md., Part No. GY012T1-Tape) was cut into 600 mm sections. Monofilament nylon of 0.016" diameter having a circular cross section was cut into pieces 50 to 80 mm long. A medical grade transfer adhesive ARCARE 7396 supplied by Adhesive Research, Inc., Glen Rock, Pa. was used to bond the two discrete materials together. A 50 to 80 mm section of transfer adhesive having a width greater than the width of the fiber was applied to the ePTFE fiber. The transfer adhesive was then cut down and sized to the width of the fiber. The backing tape of the transfer adhesive was then removed exposing a section 50 to 80 mm long of adhesive on the ePTFE. A piece of the nylon monofilament having a 0.016 inch diameter was placed centrally along the length of the adhesive coated ePTFE fiber, then the flat ePTFE fiber was closed around the monofilament in a cigarette wrapped fashion wrapping the external surfaces of the nylon and totally encasing it. This resulted in an article having one semi-rigid section of between 50 and 80 mm in length with the remainder of the article being flexible and essentially limp. A buckling load resistance of 30 grams was tested on the buckling load resistance test apparatus of FIGS. 6 and 7.

EXAMPLE 2

The procedure of Example 1 was used to produce additional dental floss articles, with the exception that the nylon monofilaments of varied cross sectional diameters of 0.010", 0.012", 0.015", 0.017", and 0.021" were employed. The resistance to buckling load of the semi-rigid section of each of these articles increased as the cross-section of the stiffening member increased.

EXAMPLE 3

The procedure of Example 1 was used to produce a dental floss article except that the nylon monofilament had a triangular cross-section.

EXAMPLE 4

Heat shrinkable polytetrafluoroethylene tubing from Zeus Industrial Products, Inc., Raritan, N.J., identified as TFE Teflon SUB-LITE-WALL™ AWG Size No. 34 having an inside expanded diameter of 0.020", was cut into 50 to 80 mm sections. A 1150 denier flat ePTFE fiber (obtained from W. L. Gore and Associates, Inc., Elkton, Md., Part No. GY012T1) was cut into a 600 mm section. One end of the ePTFE fiber was threaded through the heat shrink tubing leaving the tubing located at a position approximately two thirds down the length of the fiber. Both ends of the fiber were tied to a two peg aluminum stand supporting the fiber under slight tension so that it did not rest on the base of the stand. The metal stand was then placed into an oven at 350 degrees centigrade for 5 minutes to allow the tubing to shrink, per the instructions from the manufacturer. The stand containing the fiber was removed from the oven and allowed to cool to room temperature. The heat shrink tubing collapsed on itself and squeezed down on the ePTFE fiber and was mechanically held in place creating a semi-rigid section. The fiber was then cut through the heat shrink tube location to make a dental floss article having a semi-rigid portion and a flexible portion.

EXAMPLE 5

Heat shrinkable low density polyethylene tubing from Raychem Corp., Menlo Park, Calif., identified as MT2000-1 mm having an inside expanded diameter of 0.045", was cut into 50 to 80 mm sections. A 1150 denier flat ePTFE fiber (obtained from W. L. Gore and Associates, Inc., Elkton, Md., Part No. GY012T1) was cut into a 600 mm section. One end of the ePTFE fiber was threaded through the heat shrink tubing leaving the tubing located at a position approximately two thirds down the length of the fiber. Both ends of the fiber were tied to a two peg aluminum stand supporting the fiber under slight tension so that it did not rest on the base of the stand. The metal stand was then placed into an oven at 125 degrees centigrade for 1 minute to allow the tubing to shrink, per the instructions from the manufacturer. The stand containing the fiber was removed from the oven and allowed to cool to room temperature. The heat shrink tubing collapsed on itself and squeezed down on the ePTFE fiber, and was mechanically held in place creating a semi-rigid section. The fiber was then cut through the heat shrink tube location to make a dental floss article having a semi-rigid portion and a flexible portion.

EXAMPLE 6

A 1200 denier towed ePTFE fiber (obtained from W. L. Gore and Associates, Inc., Elkton, Md., Part No. WY012T1-Tow) was cut into a 600 mm section. The tow fiber was tied at both ends to a two peg aluminum stand supporting the fiber under slight tension so that it did not rest on the base of the stand. A section of fiber between 50 to 80 mm long was coated with a polyvinylidene fluoride (PVDF) dispersion obtained from Whitford Corporation, West Chester, Pa. under the trade name DYKOR® 202 Clear Topcoat. The coating was applied with a small paint brush or cotton swab. The coated fiber and a 2-peg stand were then placed into an air oven at 265 degrees centigrade for a period of 5 minutes to cure the polymer. The stand and fiber were removed from the oven and allowed to cool to room temperature. The cured polymer physically and mechanically locked the towed fiber together in the specified section and created a semi-rigid section of fiber having an oval shape with major outer diameter of 0.027" and minor outer diameter of 0.021". The fiber was then removed from the stand and cut to length. The remaining uncoated section of the fiber was then waxed.

EXAMPLE 7

The procedure of Example 6 was used to create a dental floss article, with the exception that slightly more polymer dispersion was coated onto the towed fiber prior to curing, resulting in a semi-rigid section having a major outer diameter of 0.025" and a minor outer diameter of 0.023".

EXAMPLE 8

The procedure of Example 6 was used to create a dental floss article, with the exception that slightly more polymer dispersion was coated onto the towed fiber prior to curing resulting in a semi-rigid section having a major outer diameter of 0.030" and a minor outer diameter of 0.024".

EXAMPLE 9

1150 and 2200 denier ePTFE fibers of various lengths (obtained from W. L. Gore and Associates, Inc., Elkton, Md., Part No. GY012T1 and GY012T1-Tape, respectively) were intermittently towed in discrete locations of approximately 50 to 80 mm along the length of the fiber. The towed sections were located approximately 1 meter apart from each other. The fibers were then cut into a 600 mm sections, with each section containing one towed location of 50 to 80 mm in length. These fibers were tied at both ends to a two peg aluminum stand supporting the fibers under slight tension so that they did not rest on the base of the stand. The towed sections of the fibers were coated with a polyvinylidene fluoride (PVDF) dispersion obtained from Whitford Corporation, West Chester, Pa. under the trade name DYKOR® 202 Clear Topcoat. The coating was applied with a small paint brush or cotton swab. The coated fibers on the 2-peg stand were then placed into an air oven at 265 degrees centigrade for a period of 5 minutes to cure the polymer. The stand and fibers were removed from the oven and allowed to cool to room temperature. The cured polymer physically and mechanically locked the towed fiber section together thereby creating a semi-rigid portion. The fibers were then removed from the stand and cut to length. The remaining uncoated section of the fiber was then waxed.

Table 1 shows the resistance to buckling loads of various articles as determined by the teachings herein. A preferred range for resistance to buckling for the article of the present invention was determined to be from about 10 to about 60 grams.

TABLE 1

| TESTED ARTICLE | LOAD AT CONTACTS (FGC) IN GRAMS |
| --- | --- |
| 0.010" Aluminum wire | 117 |
| 0.015" Copper wire | 250 |
| 0.026" Copper wire | 1167 |
| 0.016" diameter nylon monofilament | 16 |
| Example 1: ePTFE wrapped 0.016" dia. nylon monofilament | 30 |
| Example 4: TFE SUB-LITE-WALL ™ shrink wrapped fiber | 18 |
| Example 5: MT2000 LDPE shrink wrapped ePTFE fiber | 83 |
| Example 6: DYKOR ® 202 Clear Topcoat .021" × .027" dia. | 18 |
| Example 7: DYKOR ® 202 Clear Topcoat .023" × .025" dia. | 32 |
| Example 8: DYKOR ® 202 Clear Topcoat .024" × .030" dia. | 42 |

We claim:

1. A dental floss article comprising:
   a polytetrafluoroethylene (PTFE) fiber having a length and at least one substantially rigid portion and at least one flexible portion, wherein the at least one substantially rigid portion is defined by a polymeric covering such that a length of the PTFE fiber is substantially encapsulated by said polymeric covering.

2. The device of claim 1, wherein the polymeric covering is a tube.

3. The device of claim 1, wherein the polymeric covering is a tape wrapping.

4. The device of claim 1, wherein the PTFE fiber is expanded porous polytetrafluoroethylene (ePTFE).

5. The device of claim 1, wherein the polymeric covering is comprised at least in part of PTFE.

6. The device of claim 1, wherein the PTFE fiber is a tow yarn.

7. A dental floss article comprising:
   a hydrophobic fiber having a predetermined length and defined by at least one substantially rigid portion and at least one flexible portion, the at least one substantially rigid portion being defined by a polymeric covering article that is made integral with the hydrophobic fiber such that a length of the hydrophobic fiber is completely encapsulated by said polymeric covering article.

* * * * *